United States Patent [19]

Basset et al.

[11] Patent Number: 4,550,216

[45] Date of Patent: Oct. 29, 1985

[54] CATALYST FOR THE METATHESIS OF OLEFINS

[75] Inventors: Jean M. M. Basset; Michel Leconte, both of Villeurbanne; Jean Ollivier, Arudy; Francoise Quignard, Lyons, all of France

[73] Assignee: Societe Nationale Elf Aquitaine, France

[21] Appl. No.: 621,041

[22] Filed: Jun. 15, 1984

[30] Foreign Application Priority Data

Jun. 15, 1983 [FR] France ............................ 83 09876
Jun. 8, 1984 [FR] France ............................ 84 09001

[51] Int. Cl.$^4$ .............................................. C07C 3/62
[52] U.S. Cl. .................................. 585/645; 502/102; 502/117; 502/167; 502/168; 502/171; 585/643; 585/646
[58] Field of Search ............... 585/643, 644, 645, 646; 502/102, 117, 167, 168, 171

[56] References Cited

U.S. PATENT DOCUMENTS

| | | | |
|---|---|---|---|
| 3,671,462 | 6/1972 | O'Hara et al. | 585/643 |
| 3,691,095 | 9/1972 | Kroll et al. | 585/645 |
| 3,723,563 | 3/1973 | Bradshaw | 585/644 |
| 4,010,217 | 3/1977 | Zuech | 585/645 |
| 4,248,738 | 2/1981 | Banasiak | 585/645 |
| 4,291,187 | 9/1981 | Banasiak | 585/644 |
| 4,423,275 | 12/1983 | Myers | 585/646 |

FOREIGN PATENT DOCUMENTS 1372852 11/1974 United Kingdom .............. 585/646

OTHER PUBLICATIONS

Dodd et al., J. Molecular Catalysis, 15, p. 103, (1982).
Otton et al., J. Molecular Catalysis, vol. 8, 313, (1980).
Otton et al., Information Chimie, vol. 201, (May 1980), pp. 161-168.
Kupper et al., Z. Naturforsch, vol. 31(b), 1256, (1976).

*Primary Examiner*—D. E. Gantz
*Assistant Examiner*—A. Pal
*Attorney, Agent, or Firm*—Ostrolenk, Faber, Gerb & Soffen

[57] ABSTRACT

Improved catalyst for the metathesis of olefins comprising a compound of W with a halogen and with a phenoxy group which can carry substituents. It contains 4 halogen atoms and 2 phenoxy groups per atom of W. Preferably, the phenoxy group is halogenated. This catalyst allows the more rapid carrying out of various types of metathesis reactions, when it is used as a cocatalyst in conjunction with organo-metallic compounds, particularly Al or Sn. Among others, it allows the economical preparation of pheromones. It is practically insensitive to traces of water and oxygen.

12 Claims, No Drawings

CATALYST FOR THE METATHESIS OF OLEFINS

The invention relates to an improved catalyst for the metathesis of varius olefins; it thus comprises the process of dismutation using this catalyst.

The dismutation or metathesis of olefins, while being a relatively new technique which has been in existence for only about 20 years, has given rise to a large amount of work; as it consists in the exchange of groups adjacent the double bond, between two olefin molecules, it gives the possibility of producing compounds which are difficult to synthesise by known methods; this explains the great industrial interest of this mode of reaction. Operation takes place by heterogeneous or homogeneous catalysis, the catalytic systems generally employed being based upon the transition metals, W, Mo or Re. The reaction can be written diagrammatically as follows:

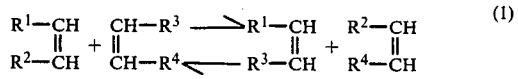
(1)

$R^1$ to $R^4$ designate carbon chains or groups, some of which can be the same and which can carry functions, such as for example carboxyls, hydroxyls, amines, nitriles, silyls, halogens, ethers or others.

In the case of homogeneous catalysis, systems are usually employed which comprise a compound such as $WCl_6$, $W(CO)_5Cl$, $W(CO)_4Cl_2$, $MoCl_5$, $Mo(NO)_2Cl_2$, $ReCl_5$ etc. in combination with an organometallic compound of the kind LiR, RMgX, $AlR_3$, $R_2AlCl_2$, $RAlCl_2$, $SnR_4$, $NaBH_4$ or the like. According to certain recent studies (H. T. DODD and K. J. RUTT, Journal of Molecular Catalysis, 15, 1982, p. 103–110), catalytic systems of particular interest comprise tetraphenoxytungsten dichlorides associated with organoaluminium compounds, particularly $C_2H_5AlCl_2$ or $(C_2H_5)_3Al_2Cl_3$. According to these authors, such systems are particularly suitable for the metathesis of olefins which do not carry functional groups, for example, for pentene-2, provided the molar ratio W/alkene is higher than 1/100 and W/Al is also as near as possible to 1/6. It is known from other studies (J OTTON, Y. COLLEULLE and J. VARAGNAT, Journal of Molecular Catalysis, 8, 1980, p. 313–324) that the very best results in the metathesis of olefins having functional groups are obtained with a catalytic system formed by $WCl_6+Sn(CH_3)_4$ where the Sn/W raio is 2.

Despite all the previous studies, industrial applications of the metathesis of olefins still suffer from certain deficiencies and require improvements. In particular, the reaction is generally too slow; on the other hand, while the components of the catalyst are recoverable, it is always preferable not to have to employ high contents of W and Al or Sn in the reaction medium, in order to reduce the costs of preparation and recovery of the catalytic system. As noted above, according to the present state of the art, substantial quantities of catalyst and co-catalyst are required. Also, catalysts based on $WCl_6$ are sensitive to traces of water and oxygen; this results in a deficiency in the constancy of catalytic activity and thus poor reproducibility of the reactions.

The present invention provides a marked improvement in that it allows considerably increased reaction speeds to be achieved, even with reduced proportions of tungsten catalyst. It also makes the metathesis much less dependent upon the W/Al or W/Sn ratio in the catalytic system utilized and insensitive to traces of water and/or oxygen.

These advantages are obtained by modification of the tungsten complex catalyst in a manner which has not been suggested in the prior art.

The improved catalyst according to the invention is characterized in that its tungsten compound comprises 4 atoms of halogen connected to the W atom and 2 phenoxy groups carried by this same atom.

This compound can be represented in a general manner by the formula:

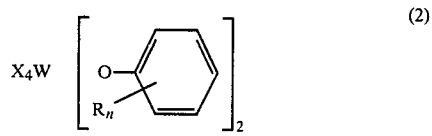
(2)

where X is a halogen, more particularly fluorine, chlorine or bromine, R being an electro-negative non-organic group or atom, particularly a halogen, $-NO_2$, $-SO_3H$, $-CN$; n can be an integral number from 1 to 5, preferably being 1 to 3.

When R is a halogen, thus representing a preferred form of the invention, it can be the same as or different from X. Particularly advantageous catalysts have the form:

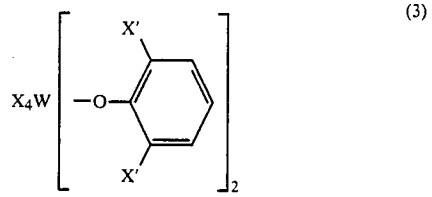
(3)

where X and X' are the same or different halogens, in particular Cl and/or Br. The position of the two X' groups ortho to the oxygen group increases the activity of the catalyst in an unexpected manner.

Various halogens, F, Cl, Br, I, can comprise the R groups.

There is no fact or principle in the art which would have indicated that catalysts of formula (2) according to the invention would be considerably more active than those of DODD and RUTT:

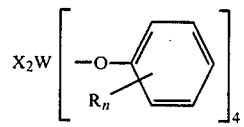

mentioned above. In effect, there was no reason to think that replacement of the 4 phenoxy groups by 2 and the 2 halogens by 4 would allow an increase in the speed of metathesis of more than 10 times, as is shown by the comparative examples given below.

Diphenoxytetrahalogenotungsten according to the invention (formula 2) is employed in association with any co-catalyst known for the purposes of metathesis, particularly one of those mentioned above in conjunction with the known art. As regards the metathesis of olefins not carrying functional groups, the preferred co-catalyst is an organoaluminium derivative or a halide of such a derivative. Thus, the compounds $R_3Al$, $RAlX_2$, $R_2AlX$ and/or $R_2Al_2X_3$ are suitable, where R is preferably a $C_1$ to $C_6$ alkyl group and X is chlorine or bromine.

However, the co-catalyst based on an organoaluminium compound has a tendency to favour secondary reactions; this disadvantage is avoided according to a particular embodiment of the invention by the use as co-catalyst of an organic compound of Sn or Pb; these co-catalysts also give improved results in the metathesis of olefins carrying functional groups.

The organic compounds of tin utilizable according to the invention are of the type $X_nSnR_{(4-n)}$, where X is a halogen and R is an alkyl group, preferably $C_1$ to $C_6$, n being 0 to 2.

Among the organic derivatives of Pb, suitable for carrying out the invention, are in particular those having the composition corresponding to the formulae:

$$PbR_m'X_{(4-m)} \text{ or } Pb_2R_m'X_{(6-m)}$$

R' being a hydrocarbon group, X a halogen and m preferably being 2 to 4 for the first formula and 2 to 6 for the second formula. The R' groups are usually $C_1$ to $C_{18}$ alkyl groups or $C_6$ to $C_{10}$ aryl groups, which may be substituted.

By way of non-limitative disclosure, the following are various organo-lead compounds utilizable according to the invention:

| | | |
|---|---|---|
| $Pb(CH_3)_4$ | $Pb(CH_3)_3F$ | $Pb(CH_3)_2Br_2$ |
| $Pb(C_2H_5)_4$ | $Pb(CH_3)_3Cl$ | $Pb(C_2H_5)_2Cl_2$ |
| $Pb(C_4H_9)_4$ | $Pb(CH_3)_3Br$ | $Pb(C_3H_7)_2Cl_2$ |
| $Pb(C_6H_5)_4$ | $Pb(CH_3)_3I$ | $Pb(C_5H_{11})_2Br_2$ |
| $Pb_2(CH_3)_6$ | $Pb(C_6H_5)_3Cl$ | $Pb(C_6H_5)_2Cl_2$ |
| $Pb_2(C_2H_5)_6$ | $Pb(C_6H_5)_3Br$ | $Pb(C_8H_{17})_2Br_2$ |
| $Pb_2(C_6H_5)_6$ | $Pb(C_4H_9)_3Cl$ | |
| $Pb_2(C_6H_{11})_6$ | $Pb(CH_3)_2Cl_2$ | |

To constitute the catalytic system according to the invention, Pb compounds are chosen which have certain solubility in the organic solvents utilizable in metathesis reaction media.

The tetra-alkyl lead compounds, particularly $C_1$ to $C_6$ alkyls, are readily available industrially and give excellent results in the dismutation of olefins according to the invention; their use in conjunction with the tungsten complexes (1) constitutes a particularly practical embodiment of the invention.

In contrast to the known art, equilibrium according to reaction (1) is attained rapidly, even with atomic ratios of Al/W very different from 6, which leads to flexibility in the industrial conduct of the process. In effect, the atomic ratios Sn/W or Pb/W in the catalytic systems according to the invention can be of the order of 0.5 to 5, preferably between 1 and 3 and most preferably from 1.5 to 2.4 with an optimum around 2.

When the metathesis concerns olefins carrying functional groups, the best co-catalyst appears to be, as indicated in the technical literature, a tetra-alkyl tin, particularly an $SnR_4'$, where R' is an alkyl group, preferably $C_1$ to $C_6$. However, according to the invention, the catalytic system is no longer $WCl_6+SnR_2'$ as in the known art, but

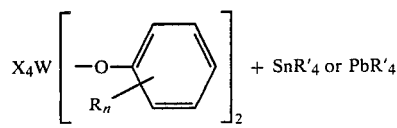

and equilibrium in the transformation of functional olefins is thus obtained very rapidly.

The improved catalysts according to the invention are usable advantageously for various types of reaction which can give rise to the metathesis of olefins. The description of such reactions can be found for example in the article by Jean OTTON published by Informations Chimie No 201, May 1980, pages 161-168. Thus, the examples of uses given below are in no way limitative of the possibilities of the new catalysts.

EXAMPLE 1

Preparation of an improved catalyst according to the invention (A)

2.5 g of $WCl_6$ ($6.33 \times 10^{-3}$ mole), 2.05 g of 2,6-dichlorophenol ($12.6 \times 10^{-3}$ mole) and 30 ml of anhydrous toluene are introduced into a 3-necked reactor, surmounted by a condensor and supplied with a stream of dry argon. After heating to 80° C. for 3 hours, a powder of a black colour is recovered, after evaporation of the toluene, and is washed with ethanol. Elementary analysis confirms the formula

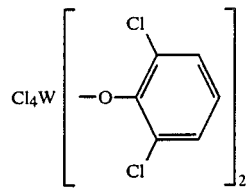

Calculation: C=22.18% H=0.93% Cl=43.66%, W=28.30%. Analysis: C=22,3% H=2.3% Cl=42.7% W=28.0%.

This catalyst is designated "A" in the following part of this description.

EXAMPLE 2

Preparation of a catalyst (B) of the prior art (DODD and RUTT cited above), considered to be one of the best.

2.5 g of $WCl_6$ ($6.3 \times 10^{-3}$ mole), 3.2 g of parachlorophenol ($25.2 \times 10^{-3}$ mole) and 30 ml of anhydrous toluene are introduced into a 3-necked reactor surmounted by a condensor and supplied with a stream of dry argon. After heating to 80° C. for 3 hours, a powder of a black colour is recovered, after evaporation of the toluene, and, after washing with ethanol, is recrystalised from a toluene-pentane mixture. Elementary analysis confirms the formula

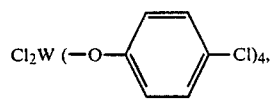

namely tetra(parachlorophenoxy)dichlorotungsten.

Calculation: C=37.65%, H=2.10%, Cl=27.84%, W=24.5%. Analysis: C=37.3% H=2.2% Cl=27.7% W=23.4%.

This catalyst is called "B" in the following examples.

EXAMPLES 3 TO 6

The tests consist in carrying out the metathesis of cis-pentene-2 according to the reaction

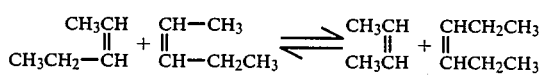

giving butene-2 and hexene-3.

The quantity of the tungsten compound (A or B) indicated in the results Table is first introduced into a reactor for discontinuous operation, previously purged with argon; then 60 ml of chlorobenzene serving as a solvent is introduced. $6 \times 10^{-4}$ mole of $C_2H_5AlCl_2$ is then added to the solution so formed.

After agitating the reactants for 5 minutes, cis-pentene-2 is introduced into the reactor in a quantity expressed as the number of moles of pentene per atom of W present.

The reactor is kept at ambient temperature. At predetermined time intervals, the gaseous phase is analysed in order to ascertain the proportion of butene formed.

It is confirmed that at 20° C., when thermodynamic equilibrium has been attained, the initial pentene-2 is converted 25% into butene-2, 25% into hexene-3 and 50% into pentene-2.

Table I below indicates the percentage of butene produced after various times for each of Examples 3 to 6.

TABLE 1

| | Example No | | | |
|---|---|---|---|---|
| | 3 | 4 | 5 | 6 |
| Catalyst | A | A | A | B |
| n-moles × $10^{-6}$ | 7 | 14 | 140 | 100 |
| Mole olefin per atom W | 3600 | 360 | 36 | 50 |
| Atoms W per 100 moles olefin | 0.028 | 0.28 | 2.8 | 2 |
| Al/W | 86 | 42.8 | 4.3 | 6 |
| Butene yield (mol %) after 5 minutes | 15.0 | 21.7 | 25.0 | 2.2 |
| 10 minutes | 20.3 | 24.9 | " | 3.7 |
| 20 minutes | 23.4 | 25.0 | " | 6.2 |
| 45 minutes | 24.0 | " | " | 10.0 |
| 120 minutes | 25.0 | " | " | 14.7 |
| 300 minutes | " | " | " | 24.8 |

It can be seen that catalyst A according to the invention gives reaction speeds which are considerably increased in comparison with that provided by catalyst B of the prior art (Example 6). In fact, equilibrium is attained after:

45 minutes in Example 3
10 minutes in Example 4
5 minutes in Example 5 while 5 hours (300 min) are required with catalyst B. Example 5 is particularly interesting due to the extreme speed of the metathesis, but even Example 3 is still entirely viable industrially, particularly in comparison with Example 6. It is thus possible to employ the improved catalyst "A" with very variable olefin/W and Al/W ratios, while remaining within the range of reaction speeds which are completely acceptable industrially.

EXAMPLE 7

Change of co-catalyst

The operations of Example 5 are repeated with the same proportions of materials, but the co-catalyst is constituted by trimethyl aluminum-sesquichloride, namely $3 \times 10^{-4}$ mole of $(CH_3)_3Al_2Cl_3$.

Equilibrium is attained in practice after 10 minutes, 24.6% of butene-2 being formed; after 5 minutes there is already 24 % of butene and this is thus close to the results of Example 5 where the co-catalyst is $C_2H_5AlCl_2$.

EXAMPLE 8

Test of a tungsten catalyst having a bromophenoxy ligand (C)

The complex compound of W of the formula:

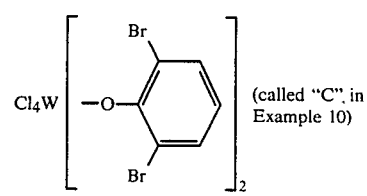

(called "C", in Example 10)

is prepared by a process analogous to that of Example 1. The metathesis of cis-pentene-2 is effected in the same manner as in Example 4, with $2.8 \times 10^{-5}$ mole (28 mg) of the compound "C" for $6 \times 10^{-4}$ mole $C_2H_5AlCl_2$ and 60 ml of chlorobenzene. Mole ratio olefin/W=360, Al/W=21.4.

After 5 minutes at ambient temperature, a yield of butene of 24% is obtained and after 30 minutes 24.3%, namely results equivalent to those of Example 4 where the phenoxy group of the catalyst A is dichlorinated.

EXAMPLES 9 TO 11

Metathesis of an olefin carrying functional groups (ethyl oleate)

The tests consist in maintaining ethyl oleate at 90° C., in the presence of a catalytic system constituted by a compound of W and tetramethyl-tin, and determining the percentage of octadecene-9 formed according to the reaction:

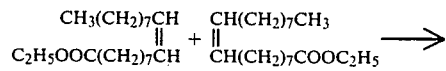

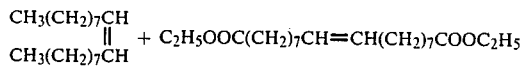

which provides at the same time ethyl-hexadecene-8-1,16-di-carboxylate.

The reaction is carried out in an apparatus for discontinuous operation, previously purged with argon, into which $2 \times 10^{-4}$ mole of the tungsten compound is introduced, followed by 5 ml of chlorobenzene as solvent and then $2 \times 10^{-4}$ mole of $Sn(CH_3)_4$.

After agitating the reactants for 15 minutes at 90° C., $0.5 \times 10^{-2}$ mole of ethyl oleate is introduced into the reactor.

The molar ratio of olefin/W is thus 50 and Sn/W=2. After predetermined time intervals, the liquid phase in the reactor is analysed, to determine the yield of octadecene-9, that is the % ratio of the number of moles of this compound formed to the number of moles of the oleate used. Table II gives the results obtained with three different catalysts: A and C according to the invention (formulae given in Examples 1 and 8) as well as $WCl_6$, generally employed in the prior art for this kind of metathesis.

TABLE II

|  | Example No | | |
| --- | --- | --- | --- |
|  | 9 | 10 | 11 |
| Catalyst | A | C | $WCl_6$ |
| Yield of octa- |  |  |  |
| decene mol %, after: |  |  |  |
| ½ hour | 6 | 10 | 4.2 |
| 1 hour | 9 | 11.5 | — |
| 2 hour | 12 | — | 5 |
| 4 hour | 13.3 | 14.5 | — |
| 20 hour | 14.5 | — | 6 |

The remarkable activity of the catalysts according to the invention is thus confirmed, as after 2 hours catalyst A provides twice the yield (12%) as that obtained with the classical $WCl_6$ (6%) only after 20 hours. Catalyst C (Br on the phenoxy group) appears to be particularly interesting, because it leads to 14.5% after only 4 hours.

EXAMPLE 12

Application of the catalyst of the invention:

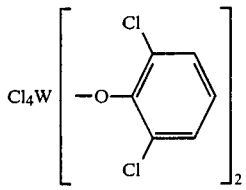

associated with $SnMe_4$ in the crossed metathesis reaction between ω-alkenyl-acetates and olefins. This is a synthesis route for insect pheromones. The reaction studied is:

$$CH_2=CH(CH_2)_3OAc + CH_3CH_2CH=CHCH_2CH_3$$
$$\text{I} \qquad\qquad\qquad \text{II}$$

-continued $$AcO(CH_2)_3CH=CH(CH_2)_3OAc +$$
$$\text{III} \qquad\qquad \text{IV}$$

$$CH_3CH_2CH=CH(CH_2)_3OAc + CH_2=CH_2 + CH_3CH_2CH=CH_2$$
$$\text{V} \qquad\qquad\qquad\qquad\qquad \text{VI}$$

In a typical experiment, the crossed metathesis reaction between 4-pentene-1-yl acetate and hexene-3 has been carried out in an apparatus of the discontinuous type, suitably purged with argon. The reactants have been introduced in the following order:

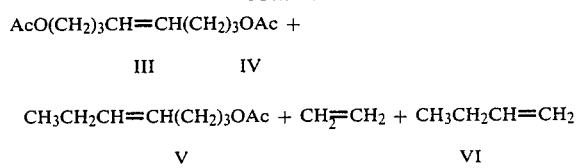

65 mg ($1.10^{-4}$ mole) of $Cl_4W$ 5 ml of chlorobenzene (solvent)
$2.10^{-4}$ mole of $SnMe_4$.

After agitating the reactants for 20 mins at 65° C., 4-pentene-1-yl acetate ($0.25 \times 10^{-2}$ mole) and hexene-3 ($0.25 \times 10^{-2}$ mole) are introduced into the reactor; the ratio (olefin+acetate)/W = 50 moles/mole. Analysis of the liquid phase effected during the period shows that, after 1 hour with the reactor at 65° C., 32% of the initial acetate has been converted and 80% after 20 hours.

Table III below gives the results obtained in the preparation of the same product by the process of the prior art utilizing $WCl_6 + SnMe_2$ as catalyst (ref *).

TABLE III

| Catalyst | Temperature | Molar ratio (I + II):W | Reaction time | Conversion of I | Selectivity of compound IV |
| --- | --- | --- | --- | --- | --- |
| $WCl_6$ + $SnMe_4$ (Ref.*) $Sn/W = 2$ | 70° C. | 10 | 16 h | 57.5% | 37% |
| 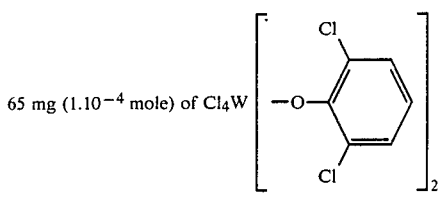 + $SnMe_4$  $Sn/W = 2$ | 65° C. | 50 | 1 h | 32% | 62% |
|  |  |  | 4 h | 52% | 75% |
|  |  |  | 20 h | 80% | 75% |

*) J LEVISALLES and D VILLEMAIN, TETRAHEDRON, 36 (1980) 3181.

The selectivity for the product IV is increased with respect to the initial acetate I.

The results obtained show that for this reaction the relevant catalyst of the present invention appears more active than the classical catalyst $WCl_6+SnMe_2$, utilisation of which in the same reaction has been described in the literature cited above.

Thus, the process of the invention shows particular utility for the manufacture of insect pheromones, industrial interest in which is increasing at the present time.

EXAMPLE 13

Use of the same catalytic system as in Example 12 for the crossed metathesis reaction between 2 terminal olefins: decene-1 and pentadecene-1. This reaction leads to the formation of tricosene-9, the cis-isomer of which is the pheromone of "musca domestica":

$$CH_2=CH(CH_2)_7CH_3 + CH_2=CH(CH_2)_{12}CH_3$$

$$\downarrow\quad\nwarrow$$

$$CH_3(CH_2)_7CH=CH(CH_2)_{12}CH_3 + CH_2=CH_2 +$$

tricosene $$CH_3(CH_2)_7CH=CH(CH_2)_7CH_3 +$$

$$CH_3(CH_2)_{12}CH=CH(CH_2)_{12}CH_3$$

See Table IV on page 16.

These results show that the catalyst of the present invention allows yields of tricosene-9 to be attained which are higher than those obtained with catalysts such as $WCl_6/EtOH/EtAlCl_2$ (reference ) or $Mo(NO)_2Cl_2(PPh_3)_2/Me_3Al_2Cl_3$; the latter system is often described in the literature as being particularly suitable for the metathesis of terminal olefins (reference *).

EXAMPLES 14 AND 15

Metathesis of an olefin carrying functional groups (ethyl oleate) with the catalyst A associated with $SnBu_4$ or $PbBu_4$.

The tests consist in maintaining ethyl oleate at 85° C., in the presence of a catalytic system constituted by catalyst A and tetrabutyl-tin or tetrabutyl-lead, and determining the percentage of octadecene-9 formed during the reaction:

TABLE IV

| Catalyst | Initial Olefins | Temperature | Reaction time (mn) | Yield (% bw) tricosene$^{-9}$ |
|---|---|---|---|---|
| $WCl_6/EtOH/EtAlCl_2$ (Ref.**) 0.1   0.3   0.5 (m mole) | octadecene-9   hexadecene-2 20 ml             4.4 ml | 50° C. | 5 | 8.6 |
| | | | 15 | 11.8 |
| | | | 30 | 11.8 |
| $Mo(NO)_2Cl_2(PPh_3)_2/Me_3Al_2Cl_3^{(a)}$ (Ref.***) 0.05                    0.6 (m mole) | decene-1/pentadecene-1 1 ml         1.35 ml | 20° C. | 15 | 6.9 |
| | | | 135 | 8.7 |
| | | | 1230 | 12.0 |
| 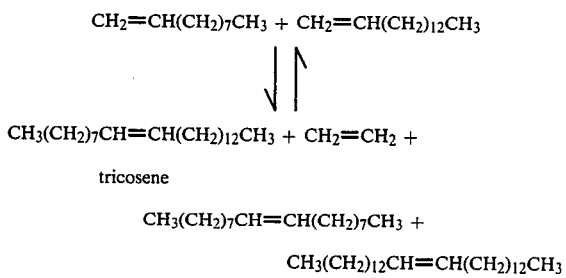 0.1                              0.2 (m mole) | decene-1/pentadecene-1 | 65° C. | 15 | 10.1 |
| | 1 ml        1.35 ml | | 45 | 16.6 |
| | | | 90 | 23.0 |
| | | | 180 | 23.0 |

$^{(a)}$Catalyst and co-catalyst in solution in 15 ml of chlorobenzene under argon; interaction for 15 minutes and then introduction of the olefins.
**F. W. KUPPER et R. STRECK, Z. Naturforsch., 31 (b) (1976) 1256
***E. A. ZUECH, W. B. HUGUES, D. H. KUBICEK et E. T. KITTLEMAN, J. Am. Chem. Soc. 92 (1970) 528

A crossed metathesis reaction between decene-1 and pentadecene-1 has been carried out in an apparatus of the discontinuous type suitably purged with argon. The reactants were introduced in the following order:

65 mg ($1.10^{-4}$ mole) of $Cl_4W$ 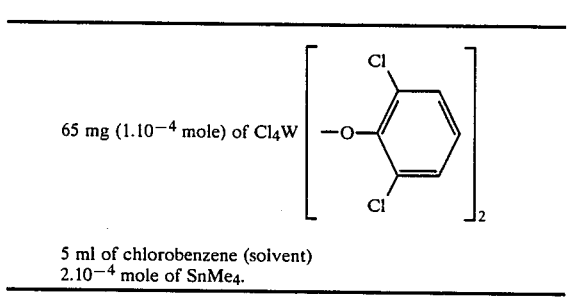

5 ml of chlorobenzene (solvent)
$2.10^{-4}$ mole of $SnMe_4$.

After agitating the reactants for 20 minutes at 65° C., decene-1 ($0.5 \times 10^{-2}$ mole) and pentadecene-1 ($0.5 \times 10^{-2}$ mole) (olefins/W=100 moles/mole) are introduced into the reactor. Analysis of the liquid phase effected during the time shows that, after 90 minutes of reaction at 65° C., a yield of 23% by weight of tricosene-9 is obtained. The results are set out in Table IV in comparison with those given by the most effective catalyst of the known art.

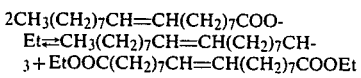

which at the same time provides ethyl-hexadecene-8-di-1,16-carboxylate.

The reaction is carried out in an apparatus for discontinuous operation previously purged with argon, into which is introduced $2 \times 10^{-4}$ mole of catalyst A, then 5 ml of chlorobenzene as solvent, $2 \times 10^{-4}$ mole of $SnBu_4$ or $PbBu_4$ and then $0.5 \times 10^{-2}$ mole of ethyl oleate. The molar ratio of olefin/W is thus 50 and Sn/W or Pb/W is 2. The reaction is carried out at 85° C. and, at given intervals of time, the liquid phase in the reactor is analysed in order to determine the yield of octadecene-9, namely the percentage ratio of the number of moles of this compound formed to the number of moles of oleate used.

Table V gives the results obtained with the two different catalytic systems: A according to the invention (formula given in Examples 1 to 8) associated with $SnBu_4$ on the one hand or with $PbBu_4$ on the other hand.

TABLE V

| | Example | |
|---|---|---|
| | 14 | 15 |
| Catalyst | A + SnBu$_4$ | A + PbBu$_4$ |
| Yield of octadecene mole % after: | | |
| ½ hour | 0 | 14% |
| 1 hour | 0 | 14% |
| 4 hours | 5% | — |
| 18 hours | 14% | — |

Comparison of these Examples 14 and 15 with Examples 9, 10 and 11 of the foregoing text shows that in this reaction, the catalysts according to the invention are more active than the classical catalyst WCl$_6$, when using SnMe$_4$, SnBu$_4$ or PbBu$_4$ as co-catalysts. A remarkable result is the very high activity of catalyst A associated with PbBu$_4$, as the maximum yield is obtained after 30 minutes, while 18 hours are required to attain this with the system A+SnBu$_4$.

EXAMPLE 16

Use of the catalyst of the invention (A), associated with PbBu$_4$, in the crossed metathesis between esters of olefin acids and olefins. This is a synthesis route for insect pheromones.

The reaction studied is:

CH$_3$(CH$_2$)$_7$CH=CH(CH$_2$)$_7$COOEt +

I

CH$_3$(CH$_2$)$_3$CH=CH(CH$_2$)$_3$CH$_3$

II

⇅

EtOOC(CH$_2$)$_7$CH=CH(CH$_2$)$_7$COOEt +

III

CH$_3$(CH$_2$)$_3$CH=CH(CH$_2$)$_7$COOEt +

IV

CH$_3$(CH$_2$)$_7$CH=CH(CH$_2$)$_7$CH$_3$ +

V

CH$_3$(CH$_2$)$_3$CH=CH(CH$_2$)$_7$CH$_3$

VI

This reaction between ethyl oleate and decene-5 has been carried out in an apparatus for discontinuous operation suitably purged with argon. The reactants were introduced in the following order:

| |
|---|
| 65 mg (1 × 10$^{-4}$ mole) of Cl$_4$W$\{$O—C$_6$H$_3$Cl$_2\}_2$ |
| 5 ml of chlorobenzene (solvent) |
| 2 × 10$^{-4}$ mole of PbBu$_4$. |

After agitating the reactants for 20 minutes at 85° C., ethyl oleate (0.375×10$^{-2}$ mole) and decene-5 (0.75×10$^{-2}$ mole) are introduced into the reactor; ratio (olefin+oleate)/W=112.5 moles/mole. Analysis of the liquid phase carried out during the time shows that, after 1 hour of reaction at 85° C., 72% of the initial oleate has been converted. Table VI below gives this result alongside the result of a preparation of the same product by the process of the prior art utilizing WCl$_6$+SnMe$_4$ as catalyst.

TABLE VI

| Catalyst | Temperature | Molar ratio (I + II):W | Reaction time | Conversion of I | Selectivity of compound IV |
|---|---|---|---|---|---|
| WCl$_6$ + SnMe$_4$ Sn/W = 2 | 85° C. | 50 | 1 h 5 h | 50% 60% | 35% 40% |
| Cl$_4$W[—O—C$_6$H$_3$Cl$_2$]$_2$ + PbBu$_4$ Pb/W = 2 | 85° C. | 112.5 | 1 h 2 h | 72% 72% | 66% 66% |

The selectivity for product IV is increased with respect to the initial oleate I.

The results obtained show that for this reaction the relevant catalyst of the present invention is much more active than the classical catalyst WCl$_6$+SnMe$_4$.

EXAMPLES 17 AND 18

Polymerisation by the metathesis of dicyclopentadiene.

In an apparatus purged with argon, discontinuous operations were carried out using the following quantities of reactants introduced in the order:

32 mg (0.5×10$^{-4}$ mole) of the same catalyst as in example 14;

20 ml of chlorobenzene as solvent

2×10$^{-4}$ mole SnBu$_4$ or 2×10$^{-4}$ mole PbBu$_4$.

After about 5 minutes at 70° C., 3.4 ml or 2.5×10$^{-2}$ mole of dicyclopentadiene is introduced. The reaction is carried out at 70° C. for 2 hours.

The following yields of polymer are then found:

| | |
|---|---|
| Example 17 co-catalyst SnBu$_4$ | 15% |
| Example 18 co-catalyst PbBu$_4$ | 45% |

EXAMPLE 19

Use of the catalyst of the invention

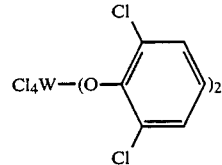

(designated above as "A"), associated with EtAlCl$_2$ or Et$_2$AlCl, in the polymerisation by metathesis of a cyclic olefin, namley dicyclopentadiene.

In two typical experiments, the polymerisation reaction of dicyclopentadiene has been carried out in an apparatus of the discontinuous type, suitably purged with argon. The reactants are introduced in the following order:

32 mg (0.5×10$^{-4}$ mole) of the W catalyst indicated, 13.5 ml of dicyclopentadiene (10$^{-1}$ mole), 6×10$^{-4}$ mole of EtAlCl$_2$ or Et$_2$AlCl in 5 ml of chlorobenzene.

The molar ratio olefin/W is thus 2,000; the ratio co-catalyst/catalyst=12; temperature 25° C.

Parallel tests under identical conditions are carried out with a catalyst of the prior art (FR No. 2180038)

constituted by tungsten tetrakis(2,6-di-isopropyl-phenate)dichloride, designated "D" in the Table below, in place of the catalyst according to the invention "A".

Results

TABLE VII

| Co-catalyst | Co-catalyst catalyst | Reaction time | Yield of polymer "A" | "D" |
|---|---|---|---|---|
| EtAlCl$_2$ | 12 | 5 s | 100% | 12% |
| " | " | 300 s | " | 100% |
| Et$_2$AlCl | 12 | 30 s | 75% | — |

It can be seen that with the catalyst of the prior art ("D") the polymerisation is much slower: it requires 300 secs there, although with catalyst "A" a total polymerisation is obtained in 5 secs.

EXAMPLE 20

Comparison of the catalyst of the invention with a catalyst of the prior art, tungsten tetrakis(2,6-di-isopropylphenate)dichloride (FR No. 2 180 038) in the metathesis reaction of cis-pentene-2.

In a reactor for discontinuous operation previously purged with argon, the quantity of the tungsten compound (catalyst of the invention or catalyst of the prior art prepared in a manner rigorously identical to the method described on page 10 of Patent No. 73 13264) indicated in the results Table; then 60 ml of chlorobenzene as solvent is introduced; $6 \times 10^{-4}$ mole of C$_2$H$_5$AlCl$_2$ is then added to the solution so formed.

After agitating the reactants for 5 minutes, cis-pentene-2 is introduced into the reactor in a quantity which is related precisely to the number of moles of pentene per atom of W present. The reactor is kept at ambient temperature. At predetermined time intervals, the gaseous phase is analysed to ascertain the proportion of butene formed. It is ascertained that at 20° C., when thermodynamic equilibrium has been realised, the initial pentene-2 is transformed 25% into butene-2, 25% into hexene-3 and 50% into pentene-2.

Table VIII below indicates the percentage of butene produced after variable times.

TABLE VIII

| Catalyst | Cl$_4$W—[O—C$_6$H$_3$Cl$_2$]$_2$ as in Example 14 | Tungsten-tetrakis-(2,6-diisopropyl phenate) dichloride (prior art) |
|---|---|---|
| n-moles × 10$^{-6}$ | 140 | 100 |
| Moles olefin per atom W | 36 | 50 |
| Atoms W per 100 moles olefin | 2.8 | 2 |
| Al/W | 4.3 | 6 |
| Yield of b tene (mol %) after: | | |
| 5 minutes | 25.0 | 0.7 |
| 20 minutes | 25.0 | 1.0 |
| 120 minutes | 25.0 | 1.5 |

It can be seen that the catalyst of the invention, in the metathesis of cis-pentene-2, gives a speed of reaction which is considerably increased in comparison with that provided by the catalyst of the prior art.

It is to be noted that the compound "A" described in Example 1 is a new chemical product.

We claim:

1. In the process for the metathesis of olefins by the contact therewith with a catalytic system comprising a compound of tungsten, the improvement which comprises employing as the compound of tungsten, a compound of the formula

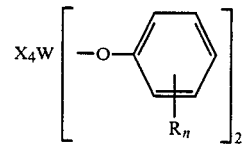

in which X is halogen, R is an electronegative group or atom, and n is an integer from 1 to 5.

2. The process of claim 1 in which X and R are individually selected from the group consisting of chlorine and bromine and n is at least 2.

3. The process of claim 2 in which there are R moieties in the ortho positions, with respect to the oxygen.

4. The process of claim 1 in which the electronegative group is —NO$_2$, —SO$_3$H, or —CN.

5. The process of claim 1 for the metathesis of olefins without functional groups in which the catalyst system contains at least one organoaluminum compound of the formula R'$_3$Al, R'AlX$_2$, R'$_2$AlX and R'$_3$Al$_2$X$_3$ in which R' is a 1 to 6 carbon atom alkyl group and X is chlorine or bromine.

6. The process of claim 1 for the metathesis of olefins containing functional groups in which the catalytic system contains an organotin compound of the formula XaSnR''$_{(4-a)}$ in which R'' is a 1 to 6 carbon atom alkyl group, X is halogen and a is 0 to 2.

7. The process of claim 6 in which a is 0.

8. The process of claim 1 in which the catalytic system contains an organic derivative of lead of the formula PbR'''$_m$X$_{(4-m)}$ or Pb$_2$R'''$_b$X$_{(6-b)}$ in which R''' is hydrocarbon group, X is halogen, m is 2 to 4 and b is 2 to 6.

9. The process of claim 8 in which R''' is 1 to 18 carbon atom alkyl group.

10. The process of claim 9 in which R''' is a 1 to 6 carbon atom alkyl group, m is 4 and b is 6.

11. The process according to claim 1 in which said compound of tungsten is di(dichlorophenoxy)tungsten tetrahalide.

12. The process of claim 1 in which said compound of tungsten is di(2,6-dichlorophenoxy)tungsten tetrachloride.

* * * * *